(12) United States Patent
Mukherjee et al.

(10) Patent No.: US 11,180,486 B2
(45) Date of Patent: Nov. 23, 2021

(54) INDOLYLKOJYL METHANE ANALOGUES, PROCESS OF PREPARATION THEREOF AND USE AS INHIBITOR OF CANCER CELLS INVASION AND METASTASIS

(71) Applicant: Council of Scientific & Industrial Research, New Delhi (IN)

(72) Inventors: Debaraj Mukherjee, Jammu (IN); Anindya Goswami, Jammu (IN); Deepak Sharma, Jammu (IN); Debasis Nayak, Jammu (IN); Shreyans Kumar Jain, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 49 days.

(21) Appl. No.: 16/626,274

(22) PCT Filed: Feb. 5, 2018

(86) PCT No.: PCT/IN2018/050060
§ 371 (c)(1),
(2) Date: Dec. 23, 2019

(87) PCT Pub. No.: WO2019/003237
PCT Pub. Date: Jan. 3, 2019

(65) Prior Publication Data
US 2020/0115365 A1 Apr. 16, 2020

(30) Foreign Application Priority Data
Jun. 27, 2017 (IN) .............................. 201711022402

(51) Int. Cl.
C07D 405/06 (2006.01)
A61K 45/06 (2006.01)

(52) U.S. Cl.
CPC ............ C07D 405/06 (2013.01); A61K 45/06 (2013.01)

(58) Field of Classification Search
CPC ............................. C07D 405/06; A61K 45/06
USPC ........................................................ 514/422
See application file for complete search history.

(56) References Cited

PUBLICATIONS

Sharma et al., "Synthesis of heteroaryl/aryl kojic acid conjugates as stimulators of gluscose uptake by GLUT4 translocation", European Journal of Medicinal Chemistry, 85, 2014, pp. 727-736.
Forouzani, Synthesis, Characterization and Catalytic Properties of Magnetic Nano Supported Molybdat Sulfuric Acid (Fe₃O₄@MSA NPs) in Base Catalyzed Synthesized of 2-Substituted aryl(amino) and (indolyl) Kojic Acid Derivatives under Solvent-free Conditions, World Journal of Organic Chemistry, 2016, pp. 1-7.
Kathiravan et al., "The biology and chemistry of antifungal agents: A review", Bioorganic & Medicinal Chemistry, 20, 2012, pp. 5678-5698.
Reddy et al., "Enantioselective 1,4-addition of kojic acid derivatives to βnitroolefins catalyzed by a cinchonine derived sugar thiourea", RSC Advances, 2014, 4, pp. 9107-9111.
Garrido et al., "Loss of GLUT4 Induces Metabolic Reprogramming and Impairs Viability of Breast Cancer Cells", Journal of Cellular Physiology, 2015, 230, 1, pp. 191-198.
Amin et al., "Par-4 Dependent Modulation of Cellular βCatenin by Medicinal Plant Natural Product Derivative 3-azido Withaferin A", Molecular Carcinogenesis, 2016, 55, pp. 864-881.
Rah et al., "A Novel MMP-2 Inhibitor 3-azidowithaferin A (3-azidoWA), Abrogates Cancer Cell Invasion and Angiogenesis by Modulating Extracellular Par-4", PLOS ONE, 2012, 7, 9, p. 44039-44039.
Lu et al., "Breast Cancer Metastasis: Challenges and Opportunities", Cancer Res, 2009, 69, 12, pp. 4951-4953.
Lee, "GRP78 Induction in Cancer: Therapeutic and Prognostic Implications",Cancer Res, 2007, 67, 8, pp. 3496-3499.
Zhao et al., "High Expression of GRP78 Promotes Invasion and Metastases in Patients with Esophageal Squamous Cell Carcinoma", Dig Dis Sci, 2015, 60, pp. 2690-2699.
Smit et al.. "The Hunt for Natural Skin Whitening Agents", Int. J. Mol. Sci., 2009, 10, pp. 5326-5349.
Reddy et al., "Indium (III), chloride catalyzed three-component coupling reaction: A novel synthesis of 2-substituted aryl(indolyl)kojic acid derivatives as potent antifungal and antibacterial agents", Bioorganic & Medicinal Chemistry Letters, 2010, 20, pp. 7507-7511.
Liu et al., "Synthesis, Characterization, and Antimicrobial Activity of Jojic Acid Grafted Chitosan Oligosaccharide", Journal of Agricultural and Food Chemistry, 2014, 62, pp. 297-303.
Rho et al., "Ester Derivatives of Kojic Acid and Polyphenols Containing Adamantane Moiety with Tyrosinase Inhibitory and Anti-inflammatory Properties", Bull. Korean Chem. Soc., 2011, 32, 4, pp. 1411-1414.
Xiong et al., "Modular Synthesis of Candidate Indole-based Insulin Mimics by Claisen Rearrangement", Organic Letters, 20089, 10, 6, pp. 1151-1154, 2008.
Nawarak et al., "Proteomics Analysis of Kojic Acid Treated A375 Human Malignant Melanoma Cells", Journal of Proteome Research, 2008, 7, pp. 3737-3746.
Yoo et al., "A modulatory effect of novel kjojic acid derivatives on cancer cell proliferation and macrophage activation", 2010, Pharmazie 65, pp. 261-266.

(Continued)

*Primary Examiner* — Kristin A Vajda
(74) *Attorney, Agent, or Firm* — Blank Rome LLP

(57) ABSTRACT

The present invention discloses novel indolylkojyl compounds of formula 1 The invention also provides a one pot, green chemistry method for preparation of indolylkojyl compounds. The compounds of the present invention are selectively toxic towards human breast cancer cells and inhibit tumor growth as well as lung metastasis. The compounds also potentiate the effect of anticancer drugs.

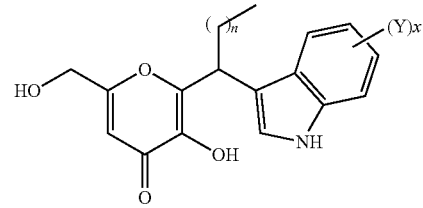

Formula 1

20 Claims, 6 Drawing Sheets

(56) References Cited

PUBLICATIONS

Sharma et al., "Synthesis of heteroaryl/aryl kojic acid conjugates as stimulators of glucose uptake by GLUT4 translocation" European Journal of Medicinal Chemistry, 85, 2014, 727-736.

Forouzani et al., "Synthesis, Characterization and Catalytic Properties of Magnetic Nano Supported Molybdat Sulfuric Acid ($Fe_3O_4$MSA NPs) in Base Catalyzed Synthesized of 2-Substituted aryl (amino) and (indolyl) Kojic Acid Derivatives under Solvent-free Conditions" World Journal of Organic Chemistry, 2016, vol. 4, No. 1, pp. 1-7.

Kathiravan et al., "The biology and chemistry of antifungal agents: A review", Bioorganic & Medicinal Chemistry, vol. 20, No. 19. 2012, pp. 5678-5698.

Reddy et al., "Enantioselective 1,4-addition of kojic acid derivatives to β-nitroolefins catalyzed by a cinchonine derived sugar thiourea", The Royal Society of Chemistry, vol. 4, No. 18. 2014, 4, pp. 9107-9111.

Garrido et al., "Loss of GLUT4 Induces Metabolic Reprogramming and impairs Viability of Breast Cancer Cells", Journal of Cellular Physiology, vol. 230. No. 1, 2015, pp. 191-198.

INDOLYLKOJYL METHANE ANALOGUES, PROCESS OF PREPARATION THEREOF AND USE AS INHIBITOR OF CANCER CELLS INVASION AND METASTASIS

RELATED APPLICATIONS

This application is a national phase application of PCT/IN2018/050060, filed Feb. 8, 2018, which claims priority to Indian Application No. 201711022402, filed Jun. 27, 2017. The entire contents of those applications are incorporated herein by reference.

FIELD OF THE INVENTION

The present invention relates to indolylkojyl methane analogs. Particularly, the present invention relates to a one pot process for preparation of indolylkojyl methane compounds using heterogeneous catalyst. The compounds of the present invention are useful as anticancer agents.

BACKGROUND AND PRIOR ART OF THE INVENTION

More than 90% of the breast cancer deaths occur due to local invasion of the cancer cells and their metastasis to distant organs like, lung and liver (Lu et al., 2009, Cancer Res. 69(12):4951-4953). GRP78 is an endoplasmic reticulum stress regulated protein overexpressed in almost all types of cancer including breast cancer. It confers tumor cells bypassing apoptosis and promotes invasion, metastasis and thus facilitates tumor growth and cancer progression (Lee., 2007, Cancer Res. 67(8):3496-3499). GRP78 has been reported to promote invasion and metastasis in most cancers by inducing matrix metalloproteases (MMP-2 and MMP-9) through suppression of the cell-cell adhesion molecule E-cadherin; whereas knockdown of GRP78 negatively affects the extracellular matrix degradation, invasion and metastasis with reduced expression of MMP-2 and MMP-9 (Zhao et al., 2015, Dig. Dis. Sci. 60(9):2690-2699). Therefore, GRP78 is regarded as an attractive target for anticancer drug discovery in academia, research sector and in industry as well.

KA is 5-Hydroxy-2-(hydroxymethyl)-4H-pyran-4-one and it has molecular formula $C_6H_6O_4$ and structure has molar mass 142.11 g/mol. The chemical structure of KA (1) is shown below. KA has been used in cosmetic biomaterials as skin lightening and bleaching agents because of its tyrosinase inhibitor activity (Smit et al., 2009, Int. J. Mol. Sci. 10(12), 5326-5349). KA also exhibits various biological activities like antimicrobial (Reddy et al., 2010, Bioorg. Med. Chem. Lett., 20(24), 7507-751; Liu et. al, 2014, J. Agric. Food Chem., 62 (1), 297-303), anti-inflammatory (Rho et al., 2011, Bull. Korean Chem. Soc., 32 (4) 1411), antidiabetic (Xiong et al., 2008, Org. Lett., 10(6), 1151-1154) and antitumour activities (Nawarak et al., 2008, J. Proteome Res. 7(9), 3737-3746). Kojic acid derivatives have their antiproliferative effects against C6 glioma cells (Yoo et al., 2010, Pharmazei. 65(4), 261-266). The proteomic analysis of the A375, human malignant melanoma cells revealed that KA treatment modulates the expression of various proteins including GRP75, VIME and 2AA that leads to the suppression of melanogenesis and tumorigenesis as well (Nawarak et al., 2008, J. Proteome Res. 7(9), 3737-3746). Using DNA microarray technology coupled to RT-qPCR, it has been reported that KA treatment to A375 cells altered a number of differentially expressed genes including seven tumor suppressor genes that were initially downregulated in melanoma cancer cells.

OBJECTIVES OF THE INVENTION

The main objective of the invention is to provide novel indolylkojyl methane analogs. Another objective of the invention is to provide novel process of preparation for indolylkojyl methane analogs from the commercially and economically available Kojic acid. Another objective of this invention is to explore the anticancer/anti-metastatic potential of active indolylkojyl methane analogue/s for the treatment of advanced diseases like; human metastatic breast cancer.

SUMMARY OF THE INVENTION

Figure 1:
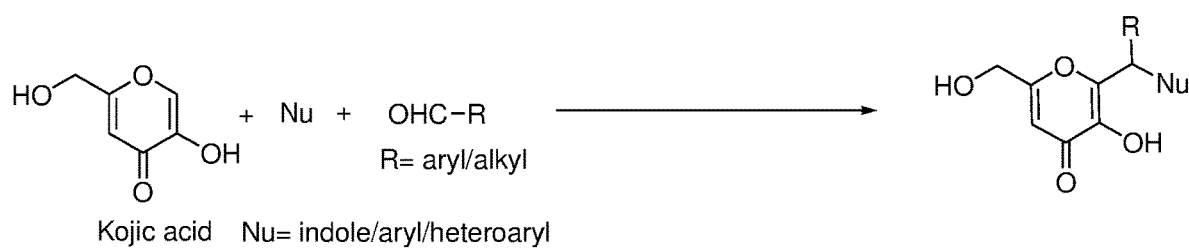
FIG. 1 is a diagram illustrating the general scheme for chemical synthesis of indolylkojyl methane analogs.

The present invention provides a compound of formula 1 or pharmaceutically acceptable salt thereof,

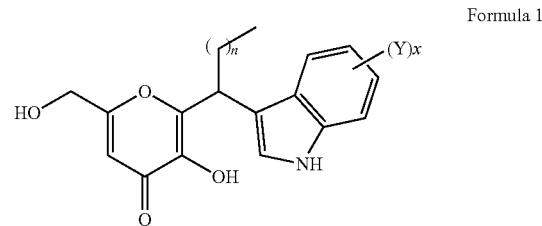

Formula 1

Y=is independently selected from the group consisting of hydrogen or substituents like independently substituted or unsubstituted alkyl or aryl, F, Cl, Br, I, CN, $NO_2$, OR, NHR, $NR_2$, $S(O)_nR$, wherein n=1-21;

R=independently substituted or unsubstituted alkyl or aryl;

n=0-2;

x=4.

In an embodiment of the present invention, wherein the alkyl group is selected from a group consisting of propyl, butyl, hexyl, heptyl, octyl, decyl, undecyl, dodecyl, hexadecyl and octadecyl.

In another embodiment of the present invention, wherein the representative compounds are:

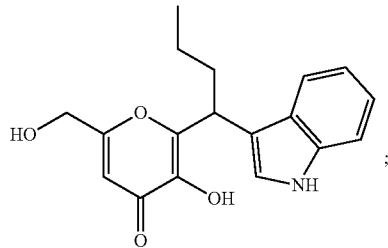

2-(1-(1H-indol-3-yl)butyl)-3-hydroxy-6-(hydroxymethyl)-4H-pyran-4-one

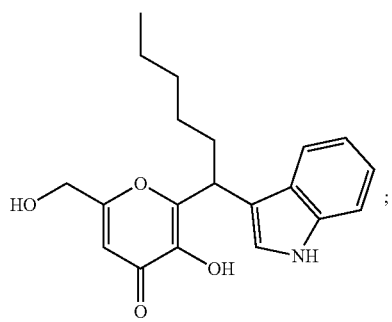

2-(1-(1H-indol-3-yl)hexyl)-3-hydroxy-6-(hydroxymethyl)-4H-pyran-4-one

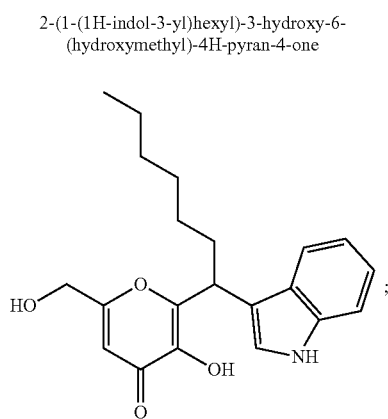

2-(1-(1H-indol-3-yl)heptyl)-3-hydroxy-6-(hydroxymethyl)-4H-pyran-4-one

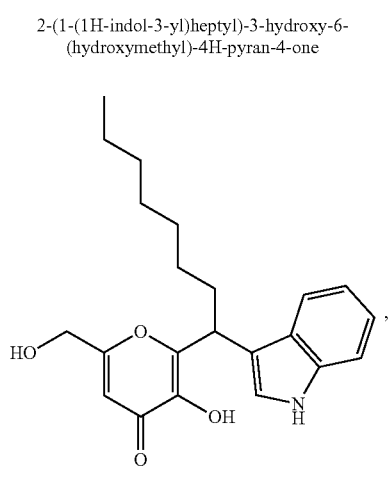

2-(1-(1H-indol-3-yl)octyl)-3-hydroxy-6-(hydroxymethyl)-4H-pyran-4-one

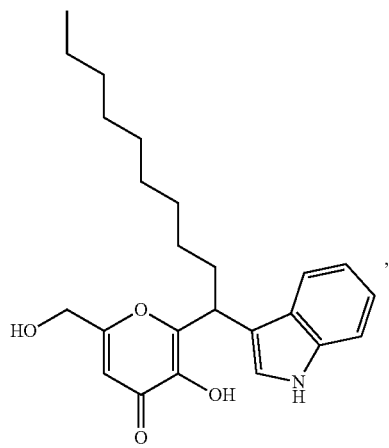

2-(1-(1H-indol-3-yl)decyl)-3-hydroxy-6-(hydroxymethyl)-4H-pyran-4-one

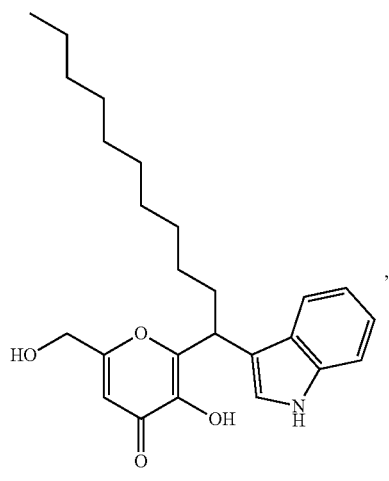

2-(1-(1H-indol-3-yl)undecyl)-3-hydroxy-6-(hydroxymethyl)-4H-pyran-4-one

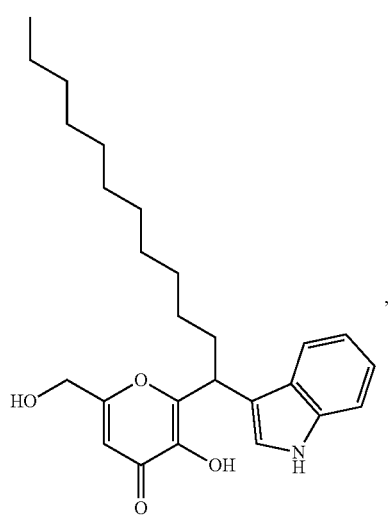

2-(1-(1H-indol-3-yl)dodecyl)-3-hydroxy-6-(hydroxymethyl)-4H-pyran-4-one

-continued

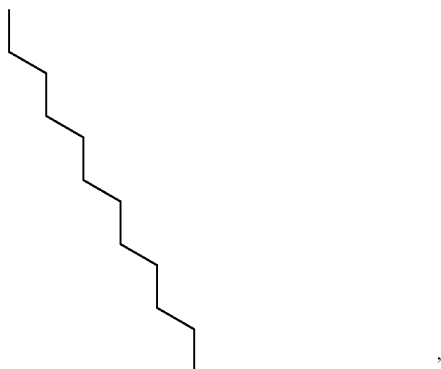

2-(1-(1H-indol-3-yl)hexadecyl)-3-hydroxy-6-(hydroxymethyl)-4H-pyran-4-one

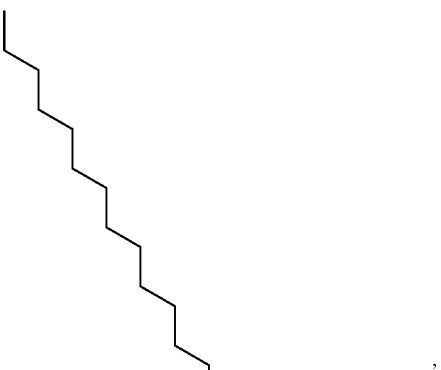

2-(1-(1H-indol-3-yl)octadecyl)-3-hydroxy-6-(hydroxymethyl)-4H-pyran-4-one

In yet another embodiment of the present invention, wherein the compounds of formula 1 for use in treatment of cancer In a preferred embodiment of the present invention, wherein the said process comprising the steps:
 i. reacting kojic acid with an aldehyde and a nucleophile in presence of heterogenous clay catalyst at a temperature ranging between 60° C. to 100° C. for a period ranging between 1-4 h to obtain reaction mixture;
 ii. diluting the reaction mixture as obtained in step (i) with organic solvent, removing the catalyst from the reaction mixture followed by purification to obtain compound of Formla 1, In another preferred embodiment of the present invention, wherein the aldehyde is selected from a group consisting of butyraldehyde, heptaldehyde, octanal, undecanal, dodecyl aldehyde, tridecanal, heptadecanal, and nonadecanal.

In still another embodiment of the present invention, wherein nucleophile is selected from indole or substituted indole.

In yet another embodiment of the present invention, wherein the heterogeneous catalyst is selected from the group consisting of Fe/Al pillared clay catalyst (Fe/Al PILC) and acidic pillared clay catalyst.

In another embodiment of the present invention, wherein the acidic pillared clay catalyst is selected from the group consisting of Al/Zr PILC, Cr/Al PILC, Ti PILC, Cr/Ti PILC and Cu/Ti PILC.

In one more embodiment of the present invention, a pharmaceutical composition comprising a compound of formula-1 or pharmaceutical acceptable salts and pharmaceutically acceptable excipients.

In yet another embodiment of the present invention, wherein the composition further comprises an anticancer agent.

In another embodiment of the present invention, wherein the ratio of Formula 1 or pharmaceutical acceptable salts and anticancer agent is 1:1 to 1:5.

In still another embodiment of the present invention, wherein the anticancer agent used is selected from a group consisting of doxorubicin, epirubicin, daunorubicin, paclitaxel, docetaxel, 5-fluorouracil, gemcitabine, carboplatin.

In a preferred embodiment of the present invention, wherein the anticancer agent is doxorubicin.

In another preferred embodiment of the present invention, wherein the ratio of compound of formula-1 and anticancer agent (doxorubicin) is 1:1.

In yet another embodiment of the present invention, wherein the anticancer activity of doxorubicin is increased upto 6 fold.13.

In a preferred embodiment of the present invention, wherein the dose of anticancer drugs can be reduced to ½ or to ¼ or to ⅙ when used in combination with the compound of formula 1.

In an embodiment of the invention, wherein the compounds of formula 1 are useful for treatment of cancer, e.g.; breast cancer, prostate cancer, colon cancer.

In another embodiment of the invention, wherein the compounds of formula 1 are useful for treatment of cancer and are also useful to potentiate the effect of anticancer drugs, e.g. doxorubicin or similar drugs, when used in pharmaceutically acceptable combination therapy In a further embodiment of the present invention, wherein the heterogeneous catalyst is Fe/Al pillared clay catalyst (Fe/Al PILC) and other acidic pillared clay catalyst such as Al/Zr PILC, Cr/Al PILC, Ti PILC, Cr/Ti PILC, Cu/Ti PILC etc.

In yet another embodiment of the present invention, wherein the compounds has its promising cytotoxic potential against a panel of breast cancer cells ($IC_{50}$: 150 nM to 3.45 μM).

In still another embodiment of the present invention, wherein the compounds are selectively toxic towards breast cancer (MDA-MB-231, MCF7, and T47D) cells, whereas the compound is less/non-toxic towards normal breast epithelial (fR2) cells.

In still another embodiment of the present invention, wherein the compounds inhibit migration, invasion and scattering ability of breast cancer cells at its sub-toxic concentration.

In still another embodiment of the present invention, wherein the compounds downregulate the expression of mammalian ER chaperone protein GRP78 involved in cancer cell invasion, metastasis, disease progression and pathogenesis of cancer.

In still another embodiment of the present invention, wherein the compounds induce pro-apoptotic protein Par-4 that interacts with GRP78 at the molecular level to inhibit NF-kB and regulates MMPs, TIMP-1 and E-cadherin for suppressing invasion in breast cancer.

In still another embodiment of the present invention, wherein the compounds inhibit tumor growth (67%) and formation of metastatic lung nodules (>85%) at a dose of 30 mg/kg body weight in 4T1 mouse mammary carcinoma model.

In still another embodiment of the present invention, wherein the compounds possesses very good pharmacokinetic profile through intravenous administration into Balb/c mice; half-life ($t_{1/2}$): 0.43 h, area under the curve ($AUC_{0-\infty}$): 406.31 ng*hr/mL.

In still another embodiment of the present invention, wherein compounds are useful to potentiate the effect of anticancer drugs, e.g. doxorubicin or similar drugs, when used in pharmaceutically acceptable combination therapy.

In still another embodiment of the present invention, wherein a synergistic pharmaceutical composition comprising a compound of formula-1 and an anticancer agent in a ratio of 1:1 to 1:5 for better therapeutic efficacy.

In an embodiment of the present invention, wherein the anticancer agent used is selected from a group consisting of doxorubicin, or similar drugs used in the treatment of breast cancer such as epirubicin, daunorubicin, paclitaxel, docetaxel, 5-fluorouracil, gemcitabine, carboplatin etc.

In an embodiment of the present invention, wherein the ratio of compound of formula-1 and anticancer agent (doxorubicin) is 1:1.

In an embodiment of the present invention, wherein the anticancer activity of doxorubicin can be increased upto 6 fold.

In an embodiment of the present invention, wherein the dose of anticancer drugs can be reduced to ½ or to ¼ or to ⅙ when used in combination with the compound of formula-1.

In an embodiment of the present invention, wherein a method of treating metastasis and cancer progression comprises administering the compounds of formula-1 or pharmaceutical compositions comprising the same in association with one or more pharmaceutical excipients to a subject suffering from the disease.

DETAILED DESCRIPTION OF THE INVENTION

The present invention relates to the synthesis of novel derivatives from kojic acid (KA), which is easily commercially available and economically competent. New efficient heterogeneous catalytic protocol has been developed to assemble KA with heteroaryl compounds via Aldol condensation and subsequent nucleophilic substitution under one pot condition. The heterogeneous catalyst can be recycled upto 5 times without loss in catalytic activity. The present invention relates to the indolylkojyl compound (Compound 5), that showed potent cytotoxic effects against a panel of human breast cancer cells. The Compound 5 is a potent inhibitor of cancer cell proliferation, invasion and metastasis both in vitro as well as in vivo, and thus could be an effective therapeutics for the treatment of highly invasive breast cancer. Mechanistically, the compound (5) consistently down-modulates the expression of pro-invasive glucose regulated protein (GRP78) implicated in invasion and metastasis of various cancer cells including breast cancer. Moreover, this indolylkojyl derivative (Compound 5) attenuates the expression of various GRP78 regulated metastatic genes such as nuclear factor kB (NF-kB), matrix metalloproteinases (MMP-2 and MMP-9). Conversely, the compound is a strong inducer of anti-metastatic proteins such as Par-4, E-cadherin and TIMP-1 in a dose dependent manner. The molecule inhibits tumor growth and metastasis much more effectively compared to the parent molecule KA in mouse mammary carcinoma model. The pharmacokinetic parameters also reveal that 5 exhibit a suitable biodistribution profile. Compound 5 also potentiates the effect of anticancer drugs (doxorubicin) when treated in combination to breast cancer cells. Hence, indolylkojyl derivative (Compound 5) can be used as a monotherapy as well as in combination to curb advanced stage metastatic diseases such as human breast cancer.

The present invention discloses KA analogues (general structure I) as inhibitor of breast cancer growth, invasion and metastasis and the process for their preparation (KA analogues) thereof.

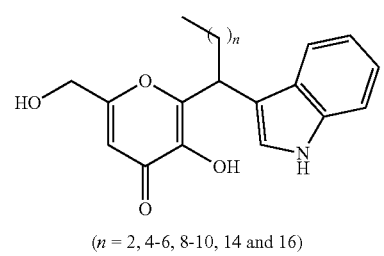

($n$ = 2, 4-6, 8-10, 14 and 16)

We have performed one step, low budget, and sustainable chemistry by using heterogeneous catalyst (Fe-Al pillared clay catalyst calcined at 425° C.) under solvent free condition. The most potent compound (5) (n=6 general structure I) evolved out of the work is novel and highly toxic against aggressive breast cancer cells ($IC_{50}$ values: 209 nM in MDA-MB-231, 150 nM in MCF7 and 3.45 µM in T47D) whereas, the compound was less/non-toxic against normal breast epithelial (fR2) cells, indicate its selectivity towards breast cancer cells. Compound 5 abrogated invasion of MDA-MB-231 and MCF7 cells at its sub-toxic concentration (200 nM) similar to the positive control doxorubicin. At the molecular level, compound 5 effectively downregulated pro-invasive, oncogenic protein GRP78 along with NF-kB, MMP-2, MMP-9 and upregulated antimetastatic Par-4, E-cadherin and TIMP-1 in a dose dependent manner. Interestingly, the compound of the invention strongly reduced tumor growth (67%) and lung metastatic nodule formation at a dose of 30 mg/kg b.w in mouse mammary carcinoma model. Moreover, compound 5 bears a very good pharmacokinetic profile claiming it as a therapeutically relevant candidate. The compound (5) can potentiate the effect of doxorubicin in breast cancer, when used in combination. In a nutshell, newly synthesized indolylkojyl methane derivative (5) is a prospective anticancer candidate to suppress tumor growth and metastasis, and hence can be used in the treatment of advanced breast cancer patients.

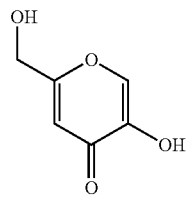

5-hydroxy-2-(hydroxymethyl)-4H-pyran-4-one; Kojic acid;

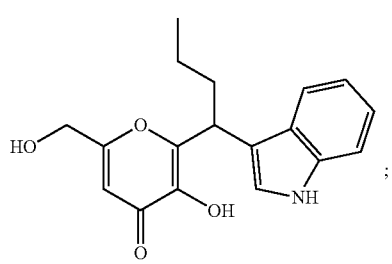

2-(1-(1H-indol-3-yl)butyl)-3-hydroxy-6-(hydroxymethyl)-4H-pyran-4-one

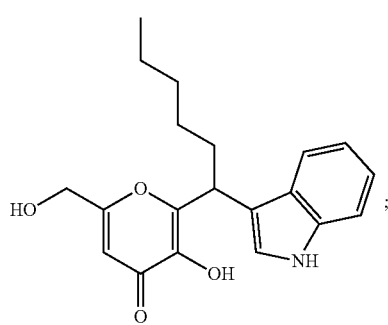

2-(1-(1H-indol-3-yl)hexyl)-3-hydroxy-6-(hydroxymethyl)-4H-pyran-4-one

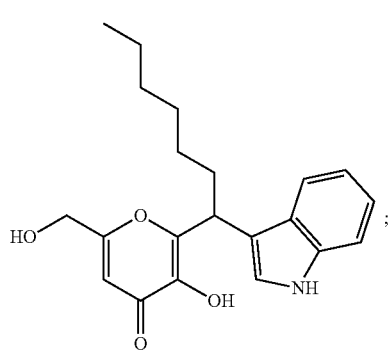

2-(1-(1H-indol-3-yl)heptyl)-3-hydroxy-6-(hydroxymethyl)-4H-pyran-4-one

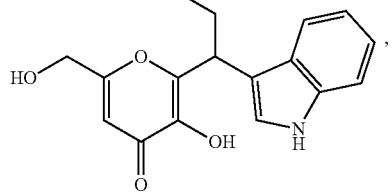

2-(1-(1H-indol-3-yl)octyl)-3-hydroxy-6-(hydroxymethyl)-4H-pyran-4-one

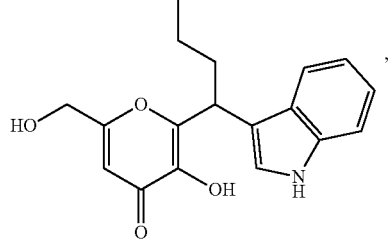

2-(1-(1H-indol-3-yl)decyl)-3-hydroxy-6-(hydroxymethyl)-4H-pyran-4-one

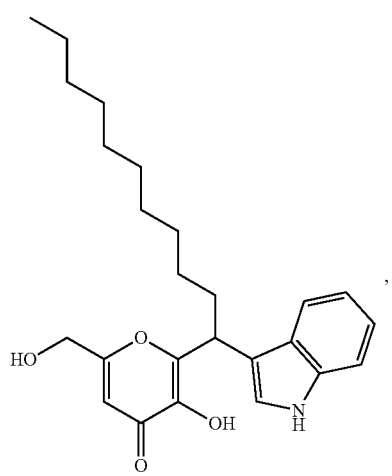

2-(1-(1H-indol-3-yl)undecyl)-3-hydroxy-6-(hydroxymethyl)-4H-pyran-4-one

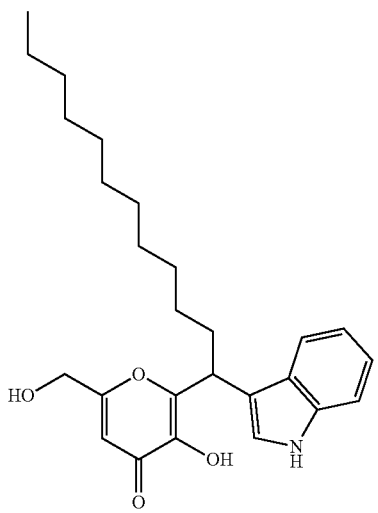

2-(1-(1H-indol-3-yl)dodecyl)-3-hydroxy-6-(hydroxymethyl)-4H-pyran-4-one

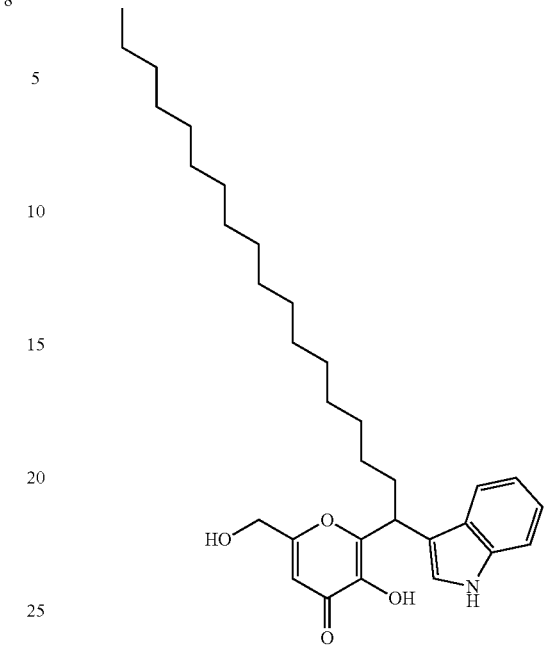

2-(1-(1H-indol-3-yl)octadecyl)-3-hydroxy-6-(hydroxymethyl)-4H-pyran-4-one

Metastatic Diseases. Human breast cancer can undergo metastatic dissemination through adoption of various processes like; epithelial-mesenchymal transition, migration, cell scattering, local invasion, intravasation into the blood stream and then extravasation to reach at a distant site/organ (preferably lungs or liver) to form secondary tumors there for the advancement of the disease. One or more compounds of the invention could be used to treat a patient (e.g. a human) at a risk of developing or already suffering from a metastatic disease, such as breast cancer.

Methods of Prevention and Treatment. The compound/s of the invention can be used to treat a patient (e.g. a human) that suffers from or is at a risk of suffering from a disease, disorder, condition, or symptom described herein. The compounds of the invention can be used and compounds in methods of treating or preventing proliferative disease such as cancer. Each such treatment described above includes the step of administering to a patient in need thereof a therapeutically effective amount of the compound of the invention described herein to delay, reduce or prevent such a disease, disorder, condition, or symptom. Besides being useful for human treatment, the compounds of the present invention could be useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

1 It is understood that the foregoing examples are merely illustrative of the present invention and should not construed to limit of the present invention. Certain modifications of the articles and/or methods employed may be made and still achieve the objectives of the invention. Such modifications are contemplated as within the scope of the claimed invention.

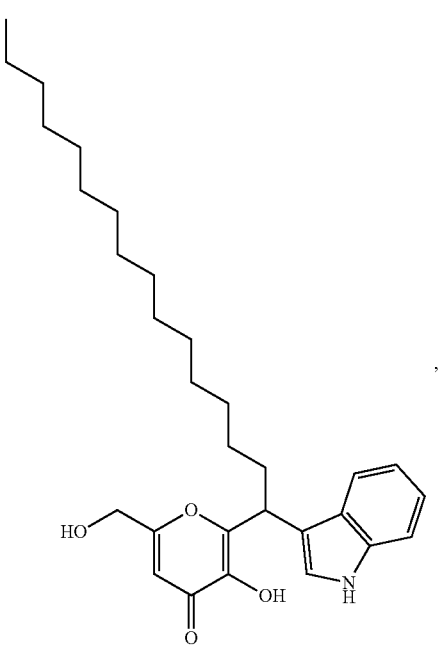

2-(1-(1H-indol-3-yl)hexadecyl)-3-hydroxy-6-(hydroxymethyl)-4H-pyran-4-one

EXAMPLES

TABLE 1

Reaction of Kojic acid (1) with various aliphatic aldehydes and indole in presence of Fe—Al pillared clay (Y)x

| Compound No. | n = | Reaction condition[b] Temp./Time | Yield (%) |
|---|---|---|---|
| 2 | 2 | 60° C./1 h | 62 |
| 2 | 2 | 70° C./1 h | 71 |
| 2 | 2 | 80° C./1 h | 75 |
| 2 | 2 | 90° C./1 h | 91 |
| 2 | 2 | 100° C./1 h | 84 |
| 3 | 4 | 90° C./1 h | 89 |
| 4 | 5 | 90° C./1 h | 88 |
| 5 | 6 | 90° C./2 h | 86 |
| 6 | 8 | 90° C./2 h | 84 |
| 7 | 9 | 90° C./2 h | 87 |
| 8 | 10 | 90° C./2 h | 85 |
| 9 | 14 | 90° C./2 h | 83 |
| 10 | 16 | 90° C./2 h | 81 |

[a]In all cases 1 equiv of Kojic acid, 1.2 equiv of aldehyde, 1 equiv of indole and 0.5 mol % of Fe—Al pilard clay calcined at 425° C. was heated with stirring at 90° C. for 1-2 h.
[b]All reactions were carried under solvent free condition.

Process of preparation of catalyst: A process for preparation of Fe/Al pillared clay catalyst wherein the catalyst is prepared by the impregnation method. $FeCl_3$ and $AlCl_3$ were diluted in distilled ethanol and stirred vigorously for one hour. Then the $H^+$ form of montmorillonite K-10 clay was added to the solution and stirred and refluxed for 15 h under a $N_2$ atmosphere and then dried under vacuum. The samples were further calcined at 425° C. to get the catalyst (Fe/Al Pillared clay-425° C.) and stored in vacuum desiccators.

Example 1. 2-(1-(1H-indol-3-yl)butyl)-3-hydroxy-6-(hydroxymethyl)-4H-pyran-4-one (2)

A mixture of Kojic acid (1 equiv.), butyraldehyde (1.2 equiv.), indole (1 equiv.) and Fe—Al pillared clay catalyst calcined at 425° C. (0.5 mol %) (Table 1, entry 1) in a test tube was heated with stirring at 90° C. for 1 h, completion of reaction was checked by TLC. After cooling, ethylacetate was added to the reaction mixture, filtered and washed (2×20 mL) to recover the catalyst. The filtrate was purified by column chromatography to afford the pure product (FIG. 1). Brown colour solid. M.pt: 130-140° C. $^1$HNMR (400 MHz, $CD_3OD$): δ0.91 (t, J=6.9 Hz, 3H), 1.21–1.53 (m, 2H), 2.03–2.33 (m, 2H), 3.33 (t, J=1.6 Hz, 1H), 4.36 (q, J=15.5 Hz, 2H), 6.42 (s, 1H), 6.99 (t, J=7.4 Hz, 1H), 7.08 (t, J=7.4 Hz, 1H), 7.23 (s, 1H), 7.33 (d, J=8.1 Hz, 1H), 7.66 (d, J=7.9 Hz, 1H); $^{13}$CNMR (125 MHz, $CD_3OD$): 176.41, 169.21, 155.66, 142.53, 137.96, 128.09, 123.39, 122.51, 119.80, 119.72, 115.61, 112.29, 109.49, 61.25, 36.12, 33.14, 23.74, 14.46. HRMS (+ESI): calcd 314.11387 and found 314.1381

Example 2. Synthesis of 2-{1-(1H-indol-3-yl)hexyl}-3-hydroxy-6-(hydroxymethyl)-4H-pyran-4-one (3)

This compound was synthesized using the similar procedure as described in example 1 (Table 1, entry 2). Brown colour solid. M.pt: 120-130° C. $^1$HNMR (400 MHz, $CD_3OD$): δ 0.77 (t, J=6.6 Hz, 3H), 1.23–1.16 (m, 6H), 2.07–2.02 (m, 2H), 3.21 (t, J=0.8 Hz, 1H), 4.23 (q, J=15.4 Hz, 2H), 6.30 (s, 1H), 6.87 (t, J=7.2 Hz, 1H), 6.97 (t, J=7.8 Hz, 1H), 7.12 (s, 1H), 7.23 (d, J=8.0 Hz, 1H), 7.65 (d, J=7.8 Hz, 1H); $^{13}$CNMR (125 MHz, $CD_3OD$): 176.43, 169.27, 155.65, 142.53, 137.96, 128.09, 123.39, 122.51, 119.80, 119.72, 115.61, 112.29, 109.52, 61.25, 36.12, 33.14, 33.01, 30.58, 30.42, 30.37, 28.75, 23.74, 14.07. HRMS (+ESI): calcd 342.1700 and found 342.1694.

Example 3. Synthesis of 2-(1-(1H-indol-3-yl)heptyl)-3-hydroxy-6-(hydroxymethyl)-4H-pyran-4-one (4)

This compound was synthesized using the similar procedure as described in example 1 (Table 1, entry 3). Brown colour solid. M.pt: 115-125° C. $^1$HNMR (400 MHz, $CD_3OD$): δ 0.77 (t, J=6.6 Hz, 3H), 1.30–1.16 (m, 8H), 2.08–2.02 (m, 2H), 3.20 (t, J=0.8 Hz, 1H), 4.21 (q, J=15.4 Hz, 2H), 6.29 (s, 1H), 6.87 (t, J=7.2 Hz, 1H), 6.97 (t, J=7.8 Hz, 1H), 7.12 (s, 1H), 7.23 (d, J=8.0 Hz, 1H), 7.65 (d, J=7.8 Hz, 1H); $^{13}$CNMR (125 MHz, $CD_3OD$): 176.39, 169.21, 155.68, 142.53, 137.96, 128.09, 123.39, 122.50, 119.80, 119.72, 115.61, 112.29, 109.52, 61.25, 36.12, 33.14, 33.01, 30.37, 28.75, 23.74, 14.46. HRMS (+ESI: calcd 356.1856 and found 356.1848.

Example 4. Synthesis of 2-{1-(1H-indol-3-yl)octyl}-3-hydroxy-6-(hydroxymethyl)-4H-pyran-4-one (5)

This compound was synthesized using the similar procedure as described in example 1 (Table 1, entry 4). Brown colour solid. M.pt: 110-120° C. $^1$HNMR (400 MHz, $CD_3OD$): δ 0.90 (t, J=6.6 Hz, 3H), 1.46–1.19 (m, 10H), 2.29–2.04 (m, 2H), 3.33 (s, 1H), 4.36 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125 MHz, $CD_3OD$): 176.41, 169.21, 155.66, 142.53, 137.96, 128.09, 123.39, 122.51, 119.80, 119.72, 115.61, 112.29, 109.52, 61.25, 36.12, 33.01, 30.58, 30.42, 30.37, 28.75, 23.74, 14.46. HRMS (+ESI): calcd 370.2013 and found 370.2005.

Example 5. Synthesis of 2-{1H-indol-3-yl)decyl}-3-hydroxy-6-(hydroxymethyl)-4H-pyran-4-one (6)

This compound was synthesized using the similar procedure as described in example 1 (Table 1, entry 5). Brown colour solid. M.pt: 110-120° C. $^1$HNMR (400 MHz, CD$_3$OD): δ 0.78 (t, J=6.6 Hz, 3H), 1.38–1.19 (m, 14H), 2.27–2.04 (m, 2H), 3.36 (s, 1H), 4.33 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125MHz, CD$_3$OD): 176.41, 169.21, 155.66, 142.53, 137.96, 128.09, 123.39, 122.51, 119.80, 119.72, 115.61, 112.29, 109.52, 61.25, 36.12, 33.01, 30.58, 30.48, 30.42, 30.37, 30.14, 28.75, 23.74, 13.46. HRMS (+ESI): calcd 398.2326 and found 398.2316.

Example 6. Synthesis of 2-{1-(1H-indol-3-yl)undecyl}-3-hydroxy-6-(hydroxymethyl)-4H-pyran-4-one (7)

This compound was synthesized using the similar procedure as described in example 1 (Table 1, entry 6). Brown colour solid. M.pt: 110-120° C. $^1$HNMR (400 MHz, CD$_3$OD): δ 0.79 (t, J=6.6 Hz, 3H), 1.46–1.17 (m, 16H), 2.29–2.02 (m, 2H), 3.31 (s, 1H), 4.36 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125 MHz, CD$_3$OD): 176.41, 169.21, 155.66, 142.53, 137.96, 128.09, 123.39, 122.51, 119.80, 119.72, 115.61, 112.29, 109.52, 61.25, 36.12, 33.01, 30.58, 30.48, 30.42, 30.37, 30.28, 30.14, 28.75, 23.74, 13.42. HRMS (+ESI): calcd 412.2482 and found 412.2470.

Example 7. Synthesis of 2-{1-(1H-indol-3-yl)dodecyl}-3-hydroxy-6-(hydroxymethyl)-4H-pyran-4-one (8)

This compound was synthesized using the similar procedure as described in example 1 (Table 1, entry 7). Brown colour solid. M.pt: 105-115° C. $^1$HNMR (400 MHz, CD$_3$OD): δ 0.78 (t, J=6.6 Hz, 3H), 1.48–1.19 (m, 18H), 2.31–2.04 (m, 2H), 3.33 (s, 1H), 4.36 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125 MHz, CD$_3$OD): 176.41, 169.21, 155.66, 142.53, 137.96, 128.09, 123.39, 122.51, 119.80, 119.72, 115.61, 112.29, 109.52, 61.25, 36.12, 33.01, 30.58, 30.48, 30.42, 30.37, 30.32, 30.28, 30.14, 28.75, 23.74, 13.37. HRMS (+ESI): calcd 426.2639 and found 426.2621.

Example 8. Synthesis of 2-{1-(1H-indol-3-yl)hexadecyl}-3-hydroxy-6-(hydroxymethyl)-4H-pyran-4-one (9)

This compound was synthesized using the similar procedure as described in example 1 (Table 1, entry 8). Brown colour solid. M.pt: 95-105° C. $^1$HNMR (400 MHz, CD$_3$OD): δ 0.79 (t, J=6.6 Hz, 3H), 1.46–1.19 (m, 26H), 2.29–2.04 (m, 2H), 3.33 (s, 1H), 4.36 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125 MHz, CD$_3$OD): 176.41, 169.21, 155.66, 142.53, 137.96, 128.09, 123.39, 122.51, 119.80, 119.72, 115.61, 112.29, 109.52, 61.25, 36.12, 33.01, 31.48, 30.58, 30.48, 30.42, 30.37, 30.32, 30.28, 30.14, 29.89, 29.54, 29.13, 28.75, 23.74, 13.29. HRMS (+ESI): calcd 482.3265 and found 482.3251.

Example 9. Synthesis of 2-{1-(1H-indol-3-yl)octadecyl}-3-hydroxy-6-(hydroxymethyl)-4H-pyran-4-one (10)

This compound was synthesized using the similar procedure as described in example 1 (Table 1, entry 9). Brown colour solid. M.pt: 90-100° C. $^1$HNMR (400 MHz, CD$_3$OD): δ 0.77 (t, J=6.6 Hz, 3H), 1.53–1.19 (m, 30H), 2.29–2.04 (m, 2H), 3.33 (s, 1H), 4.36 (q, J=15.5 Hz, 2H), 6.41 (s, 1H), 6.99 (t, J=7.4 Hz, 1H), 7.09 (t, J=7.5 Hz, 1H), 7.23 (s, 1H), 7.34 (d, J=8.1 Hz, 1H), 7.65 (d, J=7.9 Hz, 1H); $^{13}$CNMR (125 MHz, CD$_3$OD): 176.41, 169.21, 155.66, 142.53, 137.96, 128.09, 123.39, 122.51, 119.80, 119.72, 115.61, 112.29, 109.52, 61.25, 36.12, 33.01, 31.48, 30.58, 30.48, 30.42, 30.37, 30.34, 30.32, 30.28, 30.21, 30.14, 29.89, 29.54, 29.13, 28.75, 23.74, 13.35. HRMS (+ESI): calcd 510.3578 and found 510.3560.

Example 10. Cytotoxicity of the Compounds of Invention

Cell Culture and Reagents. The cell lines used in this study were procured from American Type Culture Collection (ATCC), Manassas, USA. MCF7, T47D and fR2 cells were cultured in RPMI-1640 medium, whereas the MDA-MB-231 cells were grown in Leibovitz's (L-15) medium supplemented with 10% fetal bovine serum (Gibco) and 1% penicillin/streptomycin (Sigma) in a humidified CO$_2$ incubator (New Brunswick Galaxy 170 R) with 5% CO$_2$. Reagents such as phenylmethylsulfonyl fluoride (PMSF), dithiothreitol (DTT), DMSO, crystal violet, and Bradford's reagent were purchased from Sigma-Aldrich. Protease inhibitor cocktail was procured from Roche. The antibodies for human GRP78, Par-4, MMP-2, MMP-9, NF-kB, E-cadherin and TIMP-1 were procured from Santa-Cruz Biotechnology. The β-actin antibody and the secondary antibodies such as anti-rabbit IgG and anti-mouse IgG were procured from Sigma-Aldrich.

Cell Viability Assay. The cell viability was determined by standard MTT assay method. Briefly, MDA-MB-231, MCF7, T47D and fR2 cells were seeded in 96 well tissue culture plates (Nunc) at a density of 3×10$^3$ cells per well and treated with varying concentrations of the test compounds in triplicates. DMSO was taken as a vehicle and the final concentration of the DMSO was maintained at 0.2% in the culture medium. Doxorubicin was employed as a positive control. After 44 h of incubation, MTT dye solution was added into the medium and cells were incubated for another 4 h at 37° C. in 5% CO$_2$. The amount of coloured formazan derivatives formed was measured by taking optical density (OD) using a microplate reader (TECAN, Infinite M200 Pro) at 570 nm and the percentage cell viability was calculated. The IC$_{50}$ values were calculated using GraphPad Prism software (Version 5.0). Table 2. Cytotoxicity (IC$_{50}$) of all synthesized compounds of invention against panel of human breast cancer cell lines (MDA-MB-231, MCF7, T47D) and normal breast epithelial (fR2) cells.

| Compound No. | IC$_{50}$ values (µM) | | | |
| --- | --- | --- | --- | --- |
| | MDA-MB-231 | MCF7 | T47D | fR2 |
| 1 | 87.2 ± 1.521 | 94.5 ± 2.676 | >100 | — |
| 2 | 43.25 ± 0.416 | 45.2 ± 0.348 | 43.0 ± 0.144 | — |
| 3 | 40.6 ± 0.621 | >100 | 43.5 ± 0.203 | — |
| 4 | 3.84 ± 0.055 | 3.93 ± 0.288 | 4.30 ± 0.443 | — |
| 5 | 0.209 ± 0.265 | 0.150 ± 0.095 | 3.45 ± 0.255 | 74 ± 2.6 |
| 6 | 40.6 ± 0.621 | >100 | >100 | — |
| 7 | 49.5 ± 0.448 | >100 | >100 | — |
| 8 | 45.2 ± 0.535 | >100 | >100 | — |
| 9 | 45.7 ± 0.195 | >100 | >100 | — |
| 10 | 48.5 ± 0.341 | >100 | >100 | — |
| DOXO | 0.220 ± 0.185 | 0.085 ± 0.125 | 0.081 ± 0.211 | — |

IC$_{50}$ values are indicated as mean±standard deviation of three independent experiments performed.

Compound 5 was found to be the most potent derivative among the prepared series of molecules with IC$_{50}$ values 209 nM, 150 nM and 3.45 µM in MDA-MB-231, MCF7 and T47D cells respectively, whereas the compound is less toxic towards normal breast epithelial (fR2) cells, IC$_{50}$ value 74 µM, indicating its selectivity towards breast cancer cells (Table 2).

Figure 2:
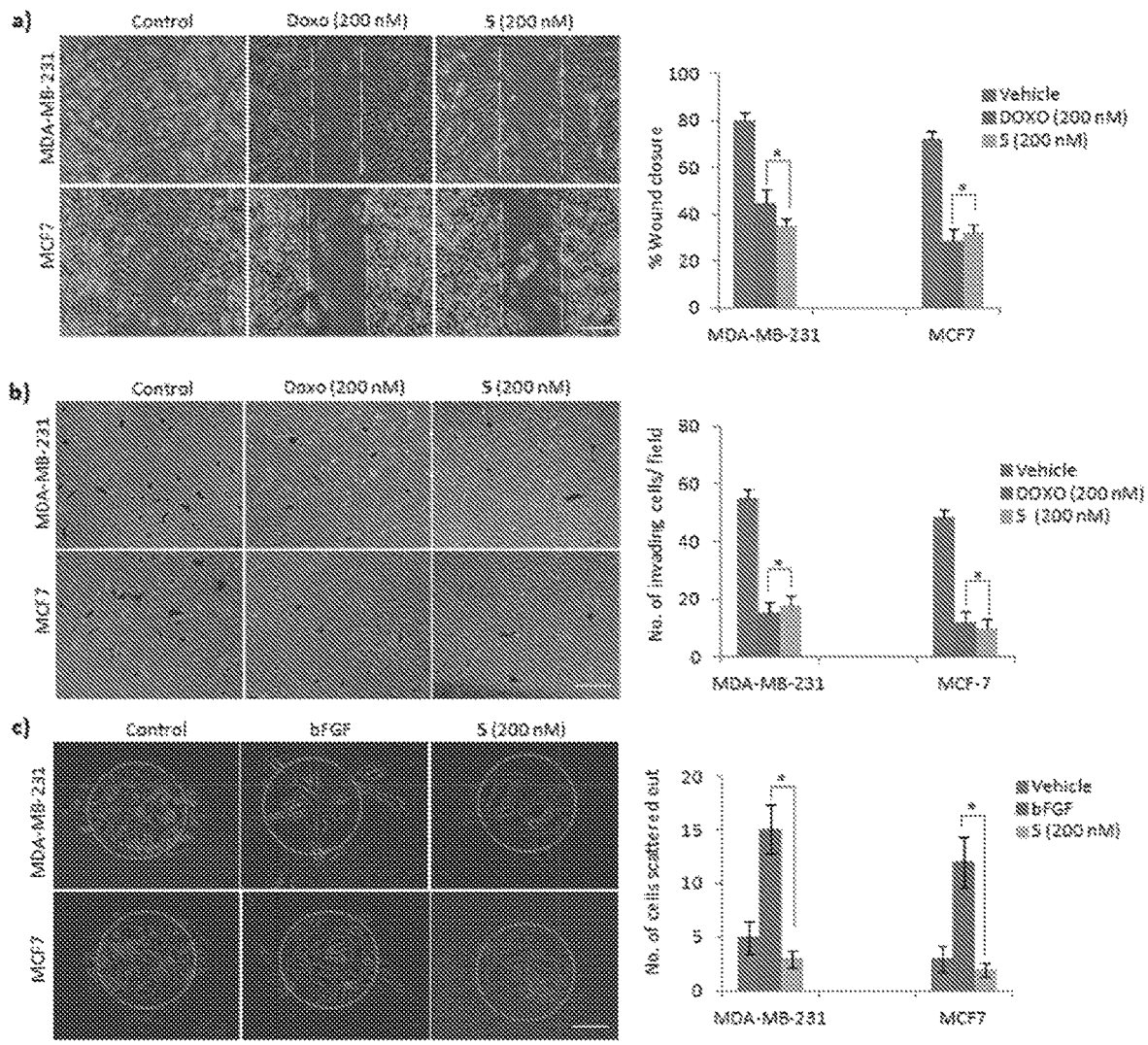
FIG. 2 is a diagram representing that compound 5 inhibits the migration, invasion and scattering ability of breast cancer cells

Example 11. Abrogation of Motility and Invasion in Breast Cancer Cells (FIG. 2)

Migration Assay. The experiment was performed according to the pre-standardized procedure (Rah et al., 2012, PloS one, 7(9). p.e44039). MDA-MB-231 and MCF7 cells were plated in 6-well plates at a concentration of (1×10$^6$ cells/well) and allowed to form a confluent monolayer for 24 h. On the next day, the monolayer was scratched with a sterile pipette tip (20-200 µl) and washed with serum free medium to remove the detached cells. Cells were subsequently treated with 5, doxorubicin and vehicle in starvation medium for another 24 h. Wounded areas were progressively photographed under an inverted microscope with Nikon D3100 camera at 20× magnification. The percentage of wound closure was estimated by the following equation: % wound closure=[1−(wound area at t1/wound area at t0)× 100], where t1 is the time after 24 h and t0 is the time immediately after giving the wound.

There observed 80% and 72% of wound closure in vehicle treated MDA-MB-231 and MCF7 cells respectively. Compound 5 suppressed migration (57.3% in MDA-MB-231 and 55.4% in MCF7) of both the invasive cells after 48 h of incubation similar to the positive control doxorubicin (FIG. 2a). Bar graphs represent quantification of percent migrating cells; error bars: mean±standard deviation three independent experiments performed, *p<0.05.

Matrigel Invasion Assay. The effect of compound 5 on invasion capability of breast cancer cells was evaluated using BD Biocoat Tumor Invasion Assay System (BD Bioscience, Bedford, Mass.) according to the manufacturer's instruction. Briefly, MDA-MB-231 and MCF7 cells (1×10$^6$) cells were cultured in the presence of 200 nM of compound 5, along with doxorubicin and vehicle for 24 h in serum free media in the upper chambers/inserts, and the bottom wells were filled with chemo-attractant (complete media with 10% FBS). Cells were allowed to migrate at 37° C. and 5% CO$_2$. After 24 h, the matrigel-coated polycarbonate filters were removed, the non-migrating cells were separated from the upper chamber with a cotton swab and the inserts were fixed with methanol and stained with 0.25% crystal violet solution. For each replicate (n=3), migration of the cells was quantified by counting the stained cells (cells per five random fields) under an inverted microscope (Amin et al., 2015, Mol. Carcinog).

The data found a 67% inhibition in MDA-MB-231 and 79% inhibition of invasion in MCF7 cells in presence of 200 nM of 5, compared to their respective control/vehicle treated cells (FIG. 2b). Bar graphs represent quantification of number of invading cells; error bars: mean±standard deviation of three independent experiments performed, *p<0.05.

Cell Scattering Assay. The procedure was followed according to the previously described method (Amin et al., 2015, Mol. Carcinog). Briefly, MDA-MB-231 and MCF7 cells were trypsinized, seeded in 6 well plates at a density of 1000 cells/well and incubated for 5 days for the formation of small colonies. On the sixth day, exhausted media was replaced by fresh media and cells were stimulated with bFGF (20 ng/mL) along with 5 (200 nM) or doxorubicin for 48 h. Cells were then washed with PBS and photographs were taken under inverted microscope at 20× magnification.

Cell scattering was significantly inhibited (80% in MDA-MB-231 and 84.5% in MCF7 cells) in cells treated with bFGF plus 5 (200 nM) compared to bFGF alone treated cells (FIG. 2c). Bar graphs represent quantification of number of cells scattered out of the colonies in each case; error bars: mean±standard deviation of three independent experiments performed, *p<0.05.

These results strongly demonstrate that compound 5 effectively abrogates migration, invasion and cell scattering in aggressive breast cancer cells.

Example 12

Figure 3:
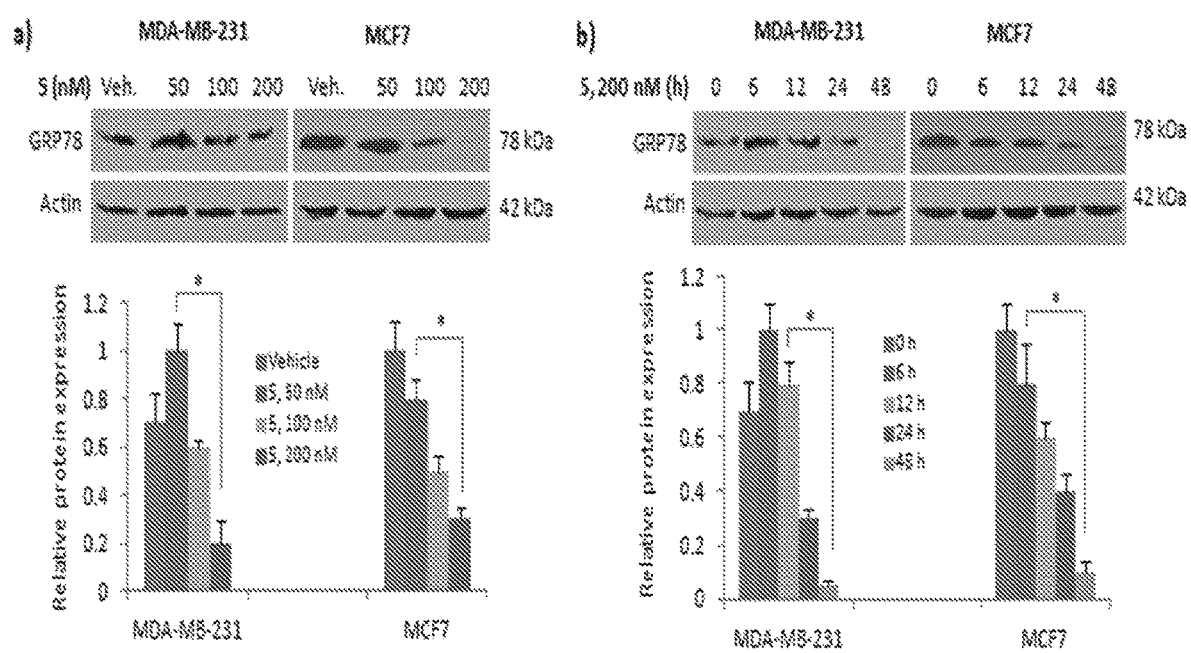
FIG. 3 is a diagram showing that compound 5 modulates the expression of GRP78 in breast cancer cells

Modulation of the Expression of GRP78 and Genes Related to Cancer Cells Invasion by Compound 5 (FIG. 3, 4)

The expression was checked through immunoblotting as described below.

Immunoblotting. MDA-MB-231 and MCF7 cells (0.5× 10$^6$) were plated in six well plates for overnight in a humidified CO$_2$ incubator and then exposed to varying concentrations of 5 (50, 100 and 200 nM) for 24 h along with vehicle (dose dependent study) and 200 nM of 5 for various time points like; 0, 6, 12, 24 and 48 h (time dependent study). Cells were then harvested, washed with chilled PBS and lysed with lysis buffer (HEPES 1 mM, KCl 60 mM, NP-40 0.3%, EDTA 1 mM, DTT 1 mM, sodium orthovanadate 1 mM, PMSF 0.1 mM and cocktail protease inhibitor). The cell extractions were centrifuged at 12,000 rpm for 10 min at 4° C. Protein concentration was measured by the standard Bradford method. An equal amount (20 µg) of protein from each sample was subjected to SDS-PAGE, and proteins were transferred to PVDF membranes (PALL), blocked with 5% (w/v) non-fat milk in PBS containing 0.1% Tween-20, probed with relevant antibodies (1:1000 dilution) for 3 h at room temperature or overnight at 4° C., and subsequently washed and probed with species-specific secondary antibodies coupled to horseradish peroxidase. Immunoreactive proteins were detected by Enhanced Chemiluminescence Plus (Thermo) (Rah et al., 2012, PloS one, 7(9), p.e44039.).

The results found a steady downregulation in the expression of GRP78 at 100 and 200 nM concentration of the molecule in both the MDA-MB-231 and MCF7 cell lines compared to the control/vehicle treated cells (FIG. 3a). There also observed a consistent decrease in the expression of intracellular GRP78 at 24 h time point and the expression was almost vanished at the 48 h time period (FIG. 3b). The graphs show the relative protein expression of GRP78 determined by densitometric analysis of the bands. The data represent three independent experiments performed, *P<0.05. Together, these results demonstrate that 5 inhibit expression of GRP78 in invasive breast cancer cells.

Figure 4:
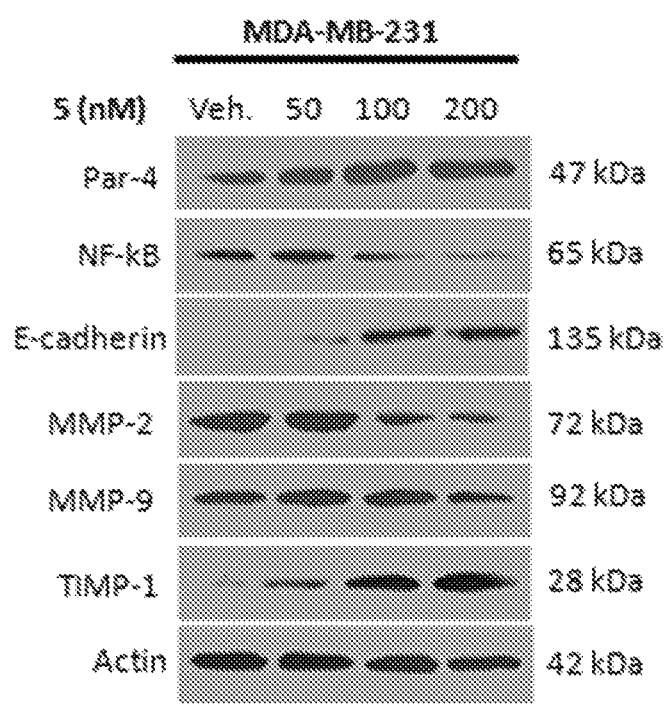
FIG. 4 is a diagram indicating that compound 5 regulates genes involved in GRP78 mediated invasion and metastasis

The expression of GRP78 signals to various oncogenic/ metastatic proteins, collectively they can aggravate the invasive capability of cancer cells. NF-kB transcription factor is regarded as an important regulator of cell proliferation and invasion collectively functions with GRP78 to facilitate MMPs. Conversely, the expression of some tumor suppressor/anti-metastatic genes (Par-4, E-cadherin, and TIMP-1) diminishes in these invasive cancer cells. Treatment with compound 5 to MDA-MB-231 cells downregulated the expression of NF-kB, MMP-2 and MMP-9, whereas the expressions of Par-4, E-cadherin and TIMP-1 induced significantly in a dose dependent manner, indicating loss of invasive ability in these cells (FIG. 4). These findings unveil how compound 5 regulates invasion and metastasis of breast cancer cells at the molecular level.

Figure 5:
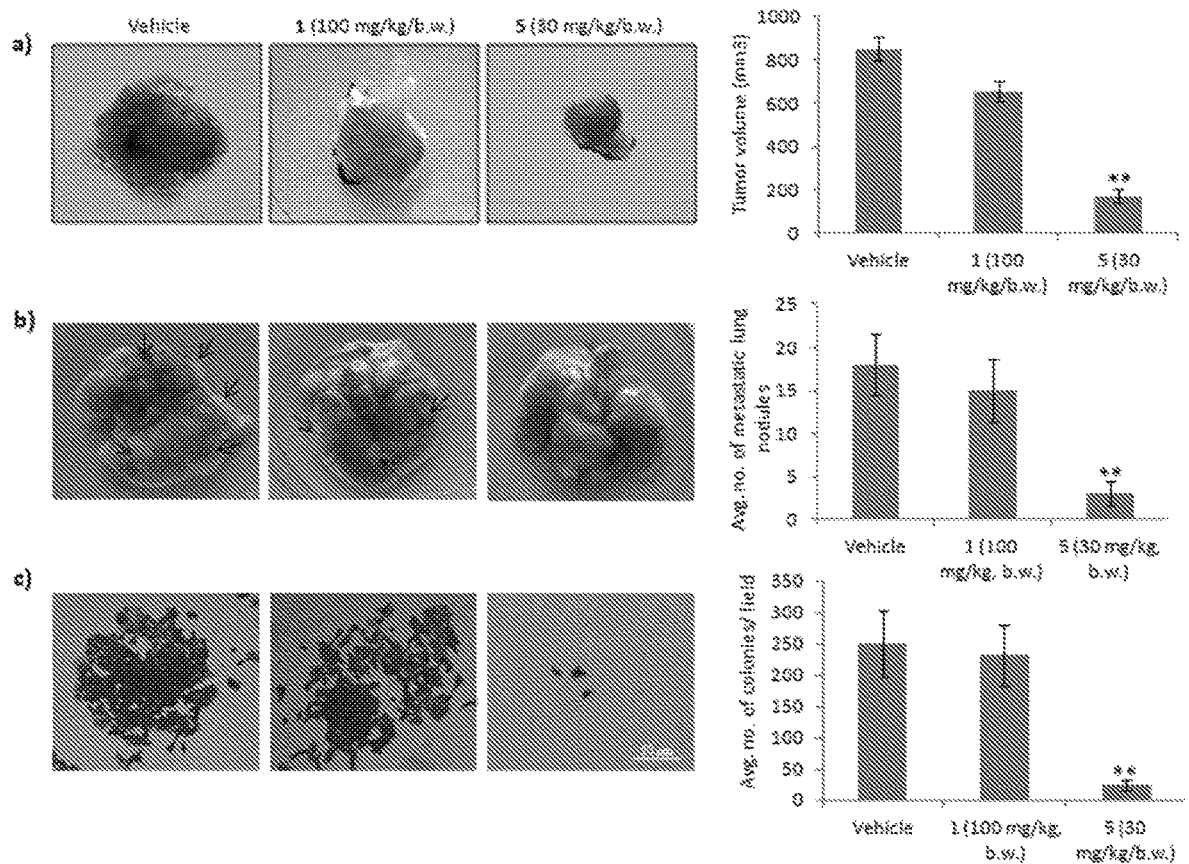
FIG. 5 is a diagram showing that compound 5 inhibits tumor growth and metastasis in vivo in murine model of metastatic breast cancer

Example 13. In Vivo Efficacy of Compound 5 (FIG. 5)

In Vivo Anti-Tumor and Anti-Metastatic Efficacy Studies. To evaluate the antitumor and antimetastatic effect of 5 in vivo, healthy female Balb/c mice (b.w. 18-23 g) were taken. The experimental protocols were approved by the Institutional Animal Ethics Committee, CPCSEA, of Indian Institute of Integrative Medicine, Jammu. The animals were maintained at 22° C. with a 12 h light-dark cycle and free access to feed and water inside the institutional animal house. Proper care was taken to maintain them in a healthy condition and to avoid any risk of possible pathogenic contaminations. For subcutaneous implantation, the mice were randomized into two groups of 5 mice per group and 1.5 million mouse mammary carcinoma (4T1) cells in serum free RPMI media were injected subcutaneously into the mammary fat pad of each mouse. Either 1 week after the tumor cell implantation or when the tumor volume reached ~150 mm$^3$, mice were injected intraperitoneally with either normal saline (NS) or parent compound 1 (100 mg/kg, b.w.) or 5 (30 mg/kg, b.w.) in each alternate days for two weeks. Tumor size was recorded on each alternate days post-cell injection and body weights were recorded once per week. Mice were sacrificed on the 15$^{th}$ day of treatment initiation and tumors were incised for its measurement. Metastatic lung nodules were counted using a dissecting microscope. Lungs were then minced into fine pieces, suspended in medium containing collagenase and kept in 37° C. incubator with vigorous shaking for 2 h. The suspension was then filtered with the help of 70 μm cell strainer (BD, USA) to get the single cell suspension. Then, the suspension was serially diluted for 3-4 times in selection medium containing 6-thioguanine, for the selection of 4T1 cells. Each dilution containing the lung cell suspension was then plated into individual petridishes and incubated at 37° C. and 5% CO$_2$ for the growing of 4T1 cell colonies. After 15 days of incubation, cells were washed with PBS, fixed with methanol and stained with 0.2% crystal violet solution for 1 h. Images of the 4T1 colonies were observed, counted and photographed under an inverted microscope at 20× magnification.

There found 79.2% inhibition in tumor growth in the group of animals treated with 5 (30 mg/kg, b.w.) compared to the control/NS treated group, whereas no significant inhibition in tumor growth was observed (23%) in 1 (100 mg/kg, b.w.) treated group of animals (FIG. 5a). The formation of metastatic lung nodules also decreased significantly 84.5% (P<0.01) in compound 5 treated group of animals compared to the 1 treated group, which had only 16.7% decrease in metastatic lung nodules (FIG. 5b). The colony formation by 4T1 cells also inhibited drastically in the lung suspension from compound 5 treated groups of animals compared to the 1 as well as vehicle treated animals (FIG. 5c). Moreover, the animals remain safe throughout the experimental period without any lethality. Together, these results demonstrate 5 inhibit tumor growth and metastasis in vivo in breast cancer model at a safe and tolerable dose of 30 mg/kg, b.w.

Example 14. Pharmacokinetic Study of Compound 5

Pharmacokinetic (PK) Study. Healthy male Balb/c mice (25-30 grams each) were taken to access the PK profile of 5. There were 11 time points for blood collection and 6 animals were there in each sampling time point for maintaining accuracy of the experiment. Animals were administered with 5, intravenously (2.5 mg/kg, b.w.) and control mice were administered with normal saline. A minimum of 100 μL of plasma was collected from each animal at different time points, viz: (0.083, 0.25, 0.5, 1, 2, 4, 6, 8, 12, 16 and 24 h) after dosing with 5 and then acetonitrile (ACN) 400 μL was added to it to precipitate the plasma proteins. The compound was extracted into the solvent, filtered and analyzed by a 6410B Triple quadrupole LC-MS/MS system (Agilent Technologies, USA). Quantification was performed through multiple reaction monitoring (MRM) separately for all the six samples collected individually at each time point by comparing with the standard calibration curve prepared using Agilent Mass Hunter software (version B.04.00). Various PK parameters like; half life ($t_{1/2}$) (h), C initial $C_0$ (ng/ml), area under the curve AUC$_{(0-\infty)}$ (ng*h/ml), $V_d$ (L/kg), Cl (L/h/kg) and Mean Residence Time (h) were calculated using non-compartmental pharmacokinetic data analysis. Following i.v. administration of a single dose of 2.5 mg/kg, b.w., $C_0$ value of 1215.67 ng/mL was achieved with an AUC$_{0-\infty}$ value of 406.31 ng*h/mL and $t_{1/2}$ was 0.43 h. The volume of distribution (Vd) and clearance (Cl) was found to be 7.61 L/kg and 12.31 L/h/kg respectively with mean residence time of 0.45 h (Table 3). The pharmacokinetic parameters of compound 5 further provide evidence that the molecule has its very good absorption and biodistribution capability through i.v. route of administration.

TABLE 3

Pharmacokinetic parameters of 5 in male Balb/c mice

| PK Parameters | Values |
| --- | --- |
| C initial (C$_0$) (ng/mL) | 1215.67 |
| Half life (t$_{1/2}$) (h) | 0.43 |
| Clearance (Cl) (L/h/kg) | 12.31 |
| Volume of distribution (Vd) (L/kg) | 7.61 |
| Area under curve (AUC$_{0-t}$) (ng*h/ml) | 395.00 |
| Area under curve (AUC$_{0-\infty}$) (ng*h/ml) | 406.31 |
| Mean residence time (MRT) (h) | 0.45 |
| Time point considered in t$_{1/2}$ calculation | 1 h-2 h |

Figure 6:
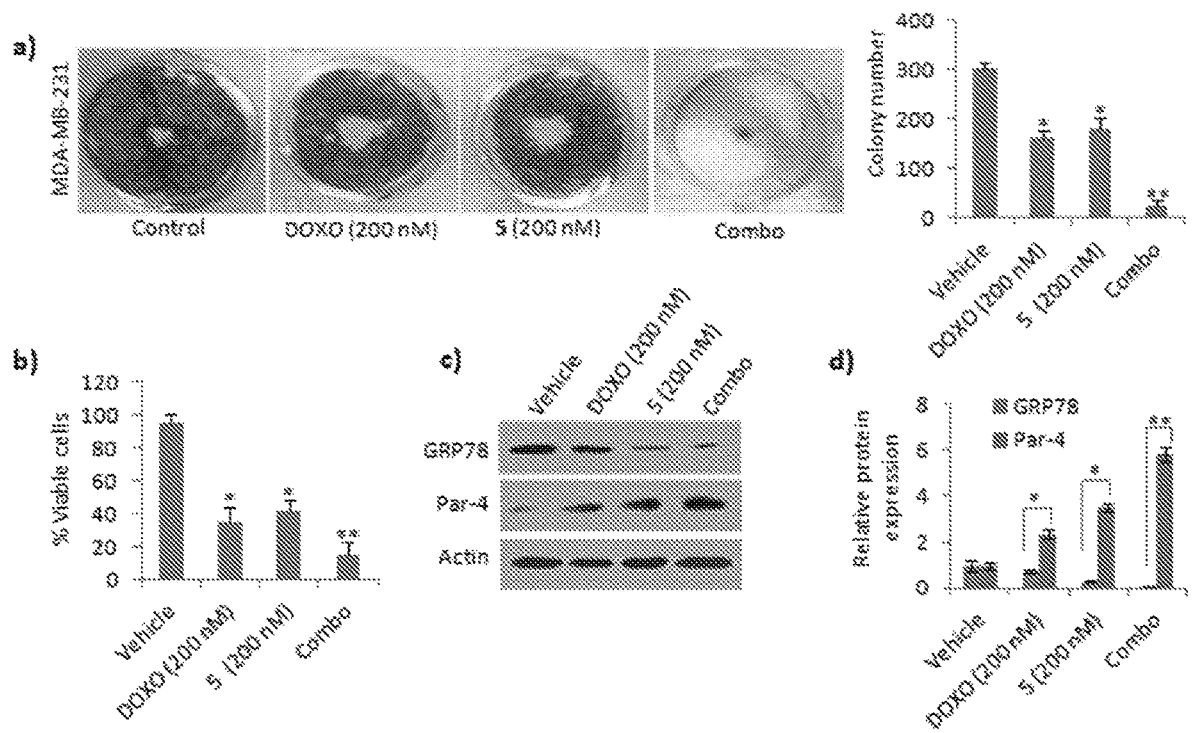
FIG. 6 is a diagram representing that compound 5 can potentiate the effect of doxorubicin when treated in combination to human breast cancer cells

Example 15. Effect of Compound 5 on Potentiation of Chemotherapeutic Drugs (FIG. 6)

Colony Formation Assay. The experiment was performed according to the pre-standardized protocol (Amin et al., 2015, *Mol. Carcinog*). Accordingly, MDA-MB-231 cells were seeded in 6 well plates at a density of 1×10$^3$ cells/well and incubated for 5 days by giving treatment with vehicle, compound 5, doxorubicin alone and/or combination of compound 5 plus doxorubicin (1:1 ratio). Cells were subsequently washed, fixed with methanol and stained with 0.2% crystal violet for 1 h. Cells were counted from atleast 3 random fields for the colony number under an inverted microscope and photographed at 20× magnifications.

Drug Potentiation Assay. Briefly, MDA-MB-231 cells were exposed to 200 nM of compound 5, 200 nM of doxorubicin alone and/or combination of both (1:1 ratio) for 48 h in cell viability (MTT) assay, for 5 days in a colony formation assay and subjected to western blotting for the expression of GRP78 and Par-4. The ability of 5 to enhance cell killing was expressed as potentiation index (PI), which was the ratio of the % inhibition of 5 alone at the given dose and the % inhibition in combination with doxorubicin. Thus, PI>1 indicates potentiation and PI<1 indicates protection.

The results found an increase in sensitivity (PI=5.2) of MDA-MB-231 cells to doxorubicin, when given in combination with 5 in a colony formation assay (FIG. 6a). This relationship was also further confirmed with the help of cell viability assay, in which also found an increased sensitization (PI=3.1) of MDA-MB -231 cells towards doxorubicin when treated in combination with 5 (FIG. 6b). Further, the western blot analysis of whole cell lysates from MDA-MB-231 cells treated with each of the molecules alone and in combination. FIG. 6c indicates that the expression of GRP78 got downregulated and almost vanished, whereas the expression of Par-4 increased robustly, when both 5 and doxorubicin given in combination for 24 h compared to the cells treated with each of the molecules alone. Densitometric analysis of western blots revealed 5.8 fold increase in the expression of Par-4 and 5.1 fold decrease in the expression of GRP78 in case of combination of both the molecules compared to each of them alone (FIG. 6d). Bar graphs represent quantification of cell viability and relative protein expression in each treatment conditions. Error bars: mean±standard deviation of three independent experiments. *P<0.05, **P<0.01. The results collectively enumerate, compound 5 significantly potentiates (upto 6 fold) the effect of doxorubicin in breast cancer and hence can be used in combination therapy along with anticancer drugs against such metastatic diseases.

ADVANTAGES OF THE INVENTION

The main advantages of the present invention are:
The present invention deals with novel one pot process for the preparation of indolylkojyl methane derivatives under heterogeneous catalysis.
The invention leads to novel potent anticancer derivative (compound 5) from commercially and economically available kojic acid.
The indolylkojyl methane compound 5 evolved out of the research possess potential anticancer activities against human breast cancer cells.
The molecule is non-toxic towards normal human breast epithelial cells, indicating 5 as a safe anticancer candidate.
Compound 5 inhibits migration, invasion, and cell scattering ability of human breast cancer cells. Hence, it can be used for the treatment of mammalian aggressive breast cancer.
The molecule (5) also found to be an effective inhibitor of tumor growth and metastasis in mouse mammary carcinoma model that can be explored further for anticancer therapeutic development.
The compound possesses a very good pharmacokinetic profile in mice, which further demonstrates its suitability as a therapeutically relevant candidate.
The compound 5 can be used as a monotherapy against advanced forms of human breast cancer. It can also potentiate the effect of doxorubicin or similar drugs used for the treatment of such metastatic diseases when used in combination.
In a nutshell, the present invention leads to the development of an anticancer drug that has the potential to block invasion and metastasis in breast cancer.

We claim:
1. A compound of Formula 1 or a pharmaceutically acceptable salt thereof,

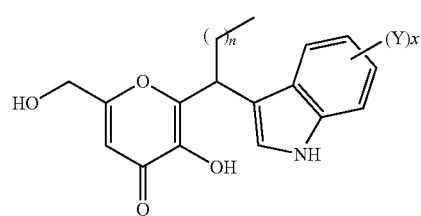

Formula 1 wherein
Y=hydrogen;
n=2, 4-6, or 8-21; and
x=4.

2. The compound of claim 1, wherein the compound is selected from:

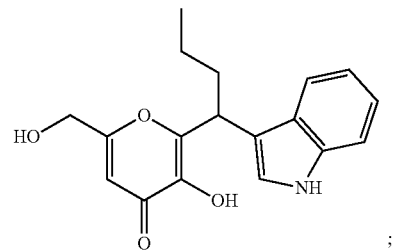

2-(1-(1H-indol-3-yl)butyl)-3-hydroxy-6-(hydroxymethyl)-4H-pyran-4-one

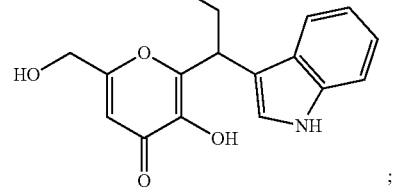

2-(1-(1H-indol-3-yl)hexyl)-3-hydroxy-6-(hydroxymethyl)-4H-pyran-4-one

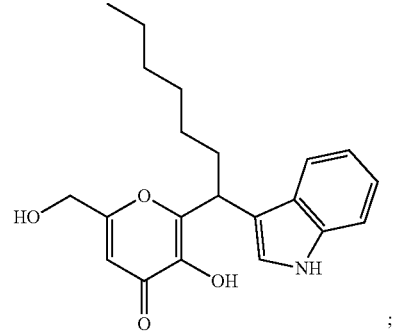

2-(1-(1H-indol-3-yl)heptyl)-3-hydroxy-6-(hydroxymethyl)-4H-pyran-4-one

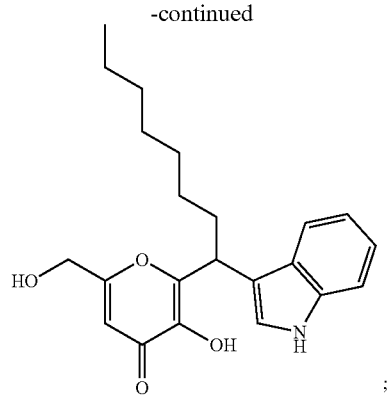
2-(1-(1H-indol-3-yl)octyl)-3-hydroxy-6-
(hydroxymethyl)-4H-pyran-4-one
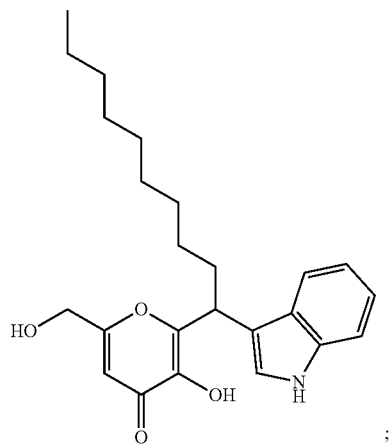
2-(1-(1H-indol-3-yl)decyl)-3-hydroxy-6-
(hydroxymethyl)-4H-pyran-4-one
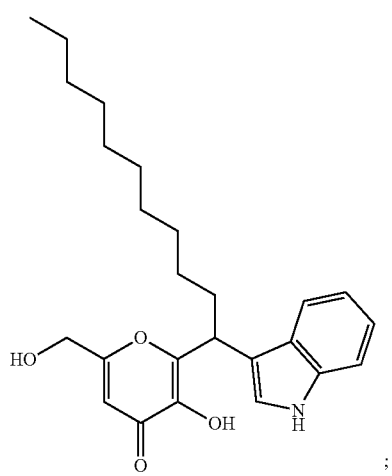
2-(1-(1H-indol-3-yl)undecyl)-3-hydroxy-6-
(hydroxymethyl)-4H-pyran-4-one
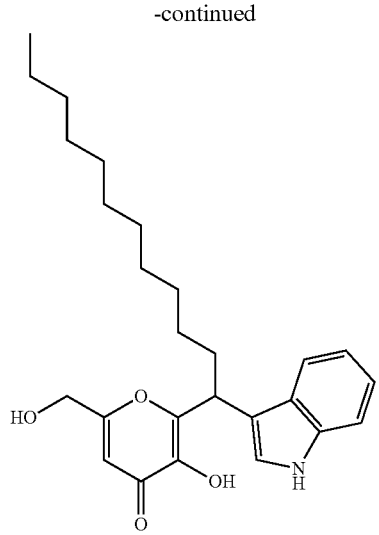
2-(1-(1H-indol-3-yl)dodecyl)-3-hydroxy-6-
(hydroxymethyl)-4H-pyran-4-one
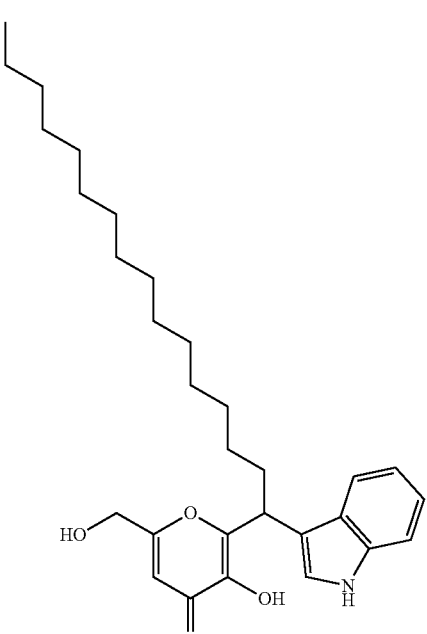
2-(1-(1H-indol-3-yl)hexadecyl)-3-hydroxy-6-
(hydroxymethyl)-4H-pyran-4-one

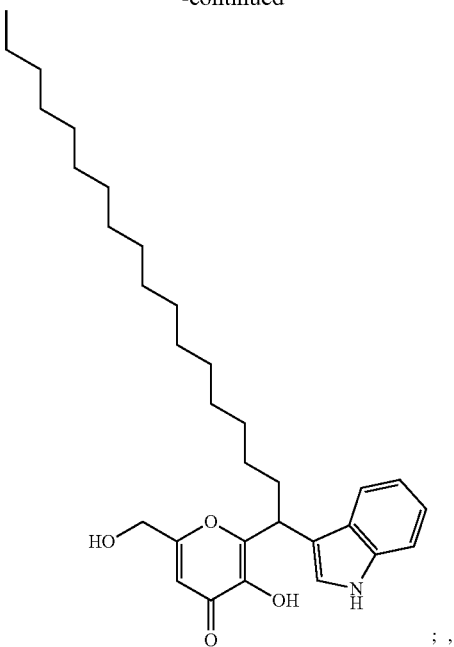

2-(1-(1H-indol-3-yl)octadecyl)-3-hydroxy-6-
(hydroxymethyl)-4H-pyran-4-one

;, and pharmaceutically acceptable salts thereof.

3. A process for the preparation of a compound according to claim 1, the process comprising:
 i. reacting kojic acid with an aldehyde and a nucleophile in the presence of a heterogenous clay catalyst at a temperature ranging between 60° C. to 100° C. for a period ranging between 1-4 h to obtain a reaction mixture; and
 ii. diluting the reaction mixture as obtained in step (i) with an organic solvent, removing the catalyst from the reaction mixture followed by purification to obtain the compound of Formula 1.

4. The process as claimed in claim 3, wherein the aldehyde is selected from a group consisting of butyraldehyde, heptaldehyde, octanal, undecanal, dodecyl aldehyde, tridecanal, heptadecanal, and nonadecanal.

5. The process as claimed in claim 3, wherein the nucleophile is selected from the group consisting of indole and substituted indoles.

6. The process as claimed in claim 3, wherein the heterogeneous clay catalyst is selected from the group consisting of Fe/Al pillared clay catalysts and acidic pillared clay catalysts.

7. The process as claimed in claim 6, wherein the acidic pillared clay catalyst is selected from the group consisting of Al/Zr pillared clay catalysts, Cr/Al pillared clay catalysts, Ti pillared clay catalysts, Cr/Ti pillared clay catalysts and Cu/Ti pillared clay catalysts.

8. A pharmaceutical composition comprising a compound according to claim 1 or pharmaceutical acceptable salts thereof and one or more pharmaceutically acceptable excipients.

9. The pharmaceutical composition of claim 8, wherein the composition further comprises an anticancer agent.

10. The pharmaceutical composition of claim 9, wherein the ratio of the compound of Formula 1 or the pharmaceutical acceptable salts thereof and the anticancer agent is 1:1 to 1:5.

11. The pharmaceutical composition of claim 8, wherein the compound is 2-(1-(1H-indol-3-yl)heptyl)-3-hydroxy-6-(hydroxymethyl)-4H-pyran-4-one or 2-(1-(1H-indol-3-yl)octyl)-3-hydroxy-6-(hydroxymethyl)-4H-pyran-4-one.

12. The compound of claim 1, wherein n is 5 or 6.

13. A method of suppressing metastasis in a patient having breast cancer, the method comprising administering a compound according to claim 1 to the patient.

14. The method of claim 13, wherein the compound is 2-(1-(1H-indol-3-yl)heptyl)-3-hydroxy-6-(hydroxymethyl)-4H-pyran-4-one or 2-(1-(1H-indol-3-yl)octyl)-3-hydroxy-6-(hydroxymethyl)-4H-pyran-4-one.

15. A method of treating breast cancer progression, the method comprising administering a compound according to claim 1 to a subject in need thereof.

16. The method of claim 15, wherein the compound is 2-(1-(1H-indol-3-yl)heptyl)-3-hydroxy-6-(hydroxymethyl)-4H-pyran-4-one or 2-(1-(1H-indol-3-yl)octyl)-3-hydroxy-6-(hydroxymethyl)-4H-pyran-4-one.

17. A method of suppressing metastasis in a patient having breast cancer, the method comprising administering a compound according to claim 8 to the patient.

18. The method of claim 17, wherein the compound is 2-(1-(1H-indol-3-yl)heptyl)-3-hydroxy-6-(hydroxymethyl)-4H-pyran-4-one or 2-(1-(1H-indol-3-yl)octyl)-3-hydroxy-6-(hydroxymethyl)-4H-pyran-4-one.

19. A method of treating breast cancer progression, the method comprising administering a pharmaceutical composition according to claim 8 to a subject in need thereof.

20. The method of claim 19, wherein the compound is 2-(1-(1H-indol-3-yl)heptyl)-3-hydroxy-6-(hydroxymethyl)-4H-pyran-4-one or 2-(1-(1H-indol-3-yl)octyl)-3-hydroxy-6-(hydroxymethyl)-4H-pyran-4-one.

* * * * *